United States Patent [19]

Miyata

[11] Patent Number: 4,562,295
[45] Date of Patent: Dec. 31, 1985

[54] METHOD OF PURIFYING CYCLOHEXANONE CONTAINING BY-PRODUCT ORGANIC ACIDS

[75] Inventor: Shigeo Miyata, Takamatsu, Japan

[73] Assignee: Kyowa Chemical Industry Co., Ltd., Tokyo, Japan

[21] Appl. No.: 637,591

[22] Filed: Aug. 3, 1984

[30] Foreign Application Priority Data

Aug. 5, 1983 [JP] Japan .................................. 58-142457

[51] Int. Cl.$^4$ ............................................. C07C 45/79
[52] U.S. Cl. .................................................. 568/366
[58] Field of Search ................................. 568/366, 410

[56] References Cited

U.S. PATENT DOCUMENTS

| 3,251,753 | 5/1966 | Mueller et al. | 568/366 |
| 3,316,302 | 4/1967 | Steeman et al. | 568/366 |
| 3,551,482 | 12/1970 | Gey et al. | 568/366 |

OTHER PUBLICATIONS

Nippon, Chem. Abst., vol. 98, #200,206g (1983).
Miyata, Chem. Abst., vol. 93, #49473r (1980).
Takezono et al., Chem. Abst., vol. 88, #74039h (1978).
Taksuya et al., Chem. Abst., vol. 88, #51696f (1978).

*Primary Examiner*—James H. Reamer
*Attorney, Agent, or Firm*—Sherman and Shalloway

[57] ABSTRACT

A method for purifying cyclohexanone containing by-product organic acids and obtained by oxidation of cyclohexane, which comprises contacting said cyclohexanone with at least one treating agent selected from the group consisting of hydrotalcite compounds of the following formula (1)

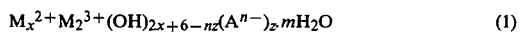

$$M_x^{2+}M_2^{3+}(OH)_{2x+6-nz}(A^{n-})_z \cdot mH_2O \tag{1}$$

wherein $M^{2+}$ represents a divalent metal ion, $M^{3+}$ represents a trivalent metal ion, $A^{n-}$ represents an anion having a valence of n, and x, z and m represent numbers satisfying the following expressions
$1 < x < 20$,
$0 < z \leq 2$,
$0 \leq m < 20'$
and metal oxide-type solid solutions of the following formula (2)

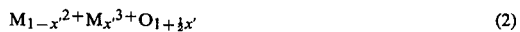

$$M_{1-x'}^{2+}M_{x'}^{3+}O_{1+\frac{1}{2}x'} \tag{2}$$

wherein $M^{2+}$ and $M^{3+}$ are as defined with respect to formula (1), and x' is a number represented by $0 < x' < 0.5$, and showing a powder X-ray diffraction pattern corresponding to $M^{2+}O$.

4 Claims, No Drawings

METHOD OF PURIFYING CYCLOHEXANONE CONTAINING BY-PRODUCT ORGANIC ACIDS

This invention relates to a method for purifying cyclohexanone containing by-product organic acids. More specifically, this invention relates to a method for removing, or removing and recovering, by-product organic acids selectively and industrially advantageously by an easy operation from cyclohexanone obtained by the oxidation of cyclohexane.

The method of this invention can obviate the alkali treatment which has been conventionally used to remove, or remove and recover, the by-product organic acids, but with many technical troubles. The method of this invention also enables the by-product organic acids to be removed, or removed and recovered, effectively by an easy operation in a simple device. According to the present invention, the treating agent can be easily reused by regeneration.

More specifically, this invention pertains to a method for purifying cyclohexanone containing by-product organic acids and obtained by oxidation of cyclohexane, which comprises contacting said cyclohexanone with at least one treating agent selected from the group consisting of hydrotalcite compounds of the following formula (1)

$$M_x{}^{2+}M_2{}^{3+}(OH)_{2x+6-nz}(A^{n-})_z \cdot mH_2O \qquad (1)$$

wherein $M^{2+}$ represents a divalent metal ion, $M^{3+}$ represents a trivalent metal ion, $A^{n-}$ represents an anion having a valence of n, and x, z and m represent numbers satisfying the following expressions
$1 < x < 20$,
$0 < z \leq 2$,
$0 \leq m < 20'$
and metal oxide-type solid solutions of the following formula (2)

$$M_{1-x'}{}^{2+}M_{x'}{}^{3+}O_{1+\frac{1}{2}x'} \qquad (2)$$

wherein $M^{2+}$ and $M^{3+}$ are as defined with respect to formula (1), and x' is a number represented by $0 < x' < 0.5$, and showing a powder X-ray diffraction pattern corresponding to $M^{2+}O$.

Cyclohexanone is useful in various applications including that as an intermediate for the synthesis of caprolactam that is used as a material for polyamides. It can be obtained by oxidizing cyclohexane. Industrially, it is produced, for example, by catalytically oxidizing cyclohexane with molecular oxygen such as air in the presence of a metal salt catalyst such as cobalt naphthenate or another catalyst In the production of cyclohexanone by the oxidation of cyclohexane, it is difficult to obtain the desired product selectively. As is well known, it involves cleavage of the main chain of cyclohexane, and in addition to cyclohexanone and cyclohexanol, various organic acids, alcohols, aldehydes, ketones, and peroxides are formed as by-products. Frequently, the amount of these by-products becomes 25 to 30% based on cyclohexane. The by-product organic acids contain relatively expensive organic acids such as adipic acid, valeric acid, caproic acid, butyric acid, succinic acid, glutaric acid and hydroxycaproic acid. Furthermore, the by-product acids form esters with cyclohexanol.

In the prior art, the oxidation product of cyclohexane is treated with an aqueous solution of an alkali such as sodium hydroxide to decompose the peroxide or esters to cyclohexanol, and the acids are separated out of the system as alkali salts in aqueous solution. Since the discarding of the spent alkali solution causes troubles, it is, for example, concentrated and burned in a boiler. Steam is recovered from the combustion gas, and sodium is recovered from the bottom of the burning furnace. Or sulfuric acid is added to the spent alkali solution to neutralize it. The tarry component composed mainly of basic acids is burned, and the aqueous layer is repeatedly extracted with a solvent. Thus, adipic acid and hydroxycaproic acid are recovered, and anhydrous sodium sulfate is recovered from the residue.

The former treatment has the industrial disadvantage that relatively expensive by-product organic acids cannot be recovered. The latter has the advantage of recovering the by-product organic acids partly. But since the treating step is long and involves complex operations, the method is industrially disadvantageous in respect of the cost of recovery.

It has now been found in accordance with this invention that by simply contacting cyclohexanone containing by-product organic acids obtained by the oxidation of cyclohexane, such as the catalytic air oxidation product of cyclohexane, with at least one treating agent selected from the group consisting of the hydrotalcite compounds of formula (1) and the metal oxide-type solid solutions of formula (2) which can be obtained as calcination products of the compounds (1), the by-product organic acids contained in cyclohexanone can be adsorbed selectively on the treating agent with high selectivity and in high yields.

It has also been discovered that the by-product organic acids captured and fixed to the treating agent can be easily removed from the treating agent by washing it with an aqueous solution of an alkali such as sodium carbonate and ammonium carbonate, or with an aqueous solution of an inorganic acid, and that the treating agent can be dissolved by using a strong acid to recover the organic acids as solids, and the acid solution of the treating agent can be treated with an alkali to regenerate the treating agent. The investigations of the present inventor have thus shown that by an easy means, the by-product organic acids can be selectively removed from the oxidation product of cyclohexane, and the treating agent can be re-used.

According to this invention, there can be provided a method for purifying cyclohexanone containing by-product organic acids, by which the by-product organic acids can be selectively removed, or removed and recovered, from the cyclohexanone, industrially advantageously by an easy operation. The method of this invention enables omission of the alkali treatment which has conventionally been used for the removal or removal and recovery of the by-product organic acids but with many technical troubles, and makes it possible to remove, or remove and recover, the by-product organic acids effectively by an easy operation in a simple device. Furthermore, the treating agent can be easily regenerated for reuse. Thus, the present invention can achieve many outstanding improvements.

It is an object of this invention to provide an excellent method for purifying cyclohexanone containing by-product organic acids.

The above and other objects and advantages of this invention will become more apparent from the following description.

According to the method of this invention, cyclohexanone containing by-product organic acids obtained by the oxidation of cyclohexane is contacted with at least one treating agent selected from the group consisting of the hydrotalcite compounds of formula (1) and the metal oxide-type solid solutions of formula (2) which shows a powder X-ray diffraction pattern corresponding to $M^{2+}O$.

In the compounds of formula (1) and (2), examples of the divalent metal ion $M^{2+}$ include $Mg^{2+}$, $Ca^{2+}$, $Zn^{2+}$, $Co^{2+}$, $Ni^{2+}$ and $Cu^{2+}$. $Mg^{2+}$ and $Zn^{2+}$ are preferred. Examples of the trivalent metal ions are $Al^{3+}$, $Fe^{3+}$, $Cr^{3+}$, $Ni^{3+}$, $Co^{3+}$ and $Mn^{3+}$. Of these, $Al^{3+}$ and $Fe^{3+}$ are preferred.

In formula (1), examples of the anion $A^{n-}$ are $Cl^-$, $Br^-$, $I^-$, $F^-$, $OH^-$, $CO_3^{2-}$, $SO_4^{2-}$, $HPO_4^{2-}$, $Fe(CN)_6^{3-}$, $CH_3COO^-$, $(COO)_2^{2-}$, a citrate ion, a tartrate ion and a benzoate ion. Of these, $OH^-$, $CO_3^{2-}$ and $Cl^-$ are preferred.

In formula (1), x, z and m are numbers which satisfy the following expressions.
$1 < x < 20$, preferably $3 \leq x \leq 8$, more preferably $4 \leq x \leq 6$;
$0 < z \leq 2$, preferably $1 \leq z \leq 2$;
$0 \leq m < 20$, preferably $0 \leq m \leq 6$.

In formula (2), x' is represented by $0 < x' < 0.5$, preferably $0 < x' < 0.4$.

The metal oxide-type solid solution of formula (2) can be obtained by calcining the hydrotalcite compound of formula (1) at a suitable temperature of up to about 900° C., for example. Since the metal of $M^{3+}$ dissolves in $M^{2+}O$, the solid solution of formula (2) shows a powder X-ray diffraction pattern corresponding to $M^{2+}O$. Usually, the lattice constant of the solid solution of formula (2) is smaller than that of $M^{2+}O$. Calcination of the hydrotalcite compound of formula (1) can be carried out usually at a temperature of about 900° C., for example about 300° to about 900° C., preferably about 400° to about 800° C., more preferably about 500° to about 700°C.

The calcination treatment may be carried out in air or under atmospheric pressure. Reduced or elevated pressures may also be used, and the calcination may also be carried out in an atmosphere of an inert gas such as $N_2$ or $CO_2$. Preferably, the calcination is carried out under reduced pressure and/or in an atmosphere of an inert gas.

In the treatment of cyclohexanone containing by-product organic acids with the aforesaid treating agent, the shape of the treating agent may be properly chosen. For example, it may be in the form of a powder, particles or granulated cylindrical or spherical pellets of various sizes. To perform the contacting treatment continuously, the use of the granulated pellets is preferred. For example, granulated pellets having an average particle diameter of about 0.5 to about 10 mm may be used. The shape and size of the granulated pellets may be changed as desired.

The manner of contacting of cyclohexanone containing by-product organic acids with the treating agent may be chosen as desired. For example, there may be employed a batchwise contacting procedure in which the cyclohexanone and the treating agent of a suitable shape and size are contacted within a suitable contacting zone with stirring or in the absence of stirring, and then the two are separated from each other; a column-type continuous one-step contacting procedure in which the cyclohexanone is passed through a column filled with the treating agent, and the treated cyclohexanone is continuously taken out; and a similar continuous multi-step contacting procedure using a multiplicity of such columns.

The temperature for the contacting treatment may be chosen properly, and is, for example, about 10° to about 300° C.

By contacting the cyclohexanone containing by-product organic acids with at least one treating agent selected from the group consisting of the hydrotalcite compounds of formula (1) and the metal oxide-type solid solutions of formula (2), the by-product organic acids can be selectively captured by the treating agent. After the contacting treatment, the removal or the removal and recovery of the by-product organic acids from the treating agent, or the regeneration and reuse of the treating agent may be carried out by easy means.

For example, the by-product organic acids adsorbed on the treating agent may be removed by washing the treating agent after the contacting treatment with an aqueous solution of an alkali. Examples of the alkali that can be used for this purpose include alkaline carbonate salts such as sodium carbonate, potassium carbonate and ammonium carbonate, alkali metal hydroxides such as sodium hydroxide and potassium hydroxide, ammonia such as aqueous ammonia and ammonia gas, and alkali metal hydrogen carbonates such as sodium hydrogen carbonate and potassium hydrogen carbonate.

According to another embodiment, the treating agent after the contacting treatment may be washed with an aqueous solution of an acid such as hydrochloric acid, nitric acid or sulfuric acid having a pH of about 0.5 to about 3 to remove the by-product organic acids. In performing this washing treatment with the acid, it is possible to use a strong acid such as hydrochloric acid, nitric acid or sulfuric acid, add an aqueous solution of the acid in an amount at least equivalent to the treating agent, and stir the mixture, thereby treating the treating agent at a temperature of, for example, about 10° to 100° C. As a result, the treating agent is dissolved and the organic acids can be recovered in the form of a solid. In this embodiment, the compound of formula (1) or (2) may be regenerated and recovered in the form of the compound of formula (1) by adding a suitable alkali such as sodium hydroxide, potassium hydroxide, sodium carbonate and aqueous ammonia to the acid solution containing the treating agent to adjust the pH of the solution to at least about 6 preferably at least about 8.

The treating agent from which the by-product organic acids have been removed as above can be re-used as such or after, as desired, it is properly calcined.

The following Examples illustrate the present invention more specifically.

EXAMPLE 1

One kilogram of a reaction solution obtained by oxidizing cyclohexane with air in the presence of cobalt naphthenate as a catalyst (containing 120 g of organic acids consisting of 1.2% by weight of butyric acid, 20.2% of valeric acid, 7.1% of caprocic acid, 1.8% of succinic acid, 3.0% of glutaric acid, 24.4% of adipic acid and 42.3% of hydroxycaproic acid) was passed through a column filled with 2 kg of cylindrical pellets, 1 mm in diameter and 2 mm in length, of a hydrotalcite compound of the composition $Mg_4Al_2(OH)_{12}CO_3 \cdot 3H_2O$. The concentration of the organic acids in the filtrate was measured and found to be 0.3 g.

Then, 5 liters of a 0.5 M aqueous solution of $Na_2CO_3$ was passed through the column filled with the hydrotalcite to ion-exchange the organic acids with $CO_3^{2-}$. The resulting filtrate contained 119 g of the organic acids.

EXAMPLE 2

A hydrotalcite compound having the composition $Mg_5Al_2(OH)_{14}CO_3 \cdot 4H_2O$ was calcined at 600° C. for 1 hour to prepare a powder of a solid solution of MgO and $Al_2O_3$ ($Mg_{5/7}Al_{2/7}O_{1 \cdot 1/7}$). 250 g of this solid solution was added to 1 kg of the same reaction solution of cyclohexane as used in Example 1. The mixture was stirred at about 70° C. for 30 minutes, and then filtered. The amount of the entire organic acids in the filtrate was 0.05 g.

Then, 1.5 liters of 10 M sulfuric acid was added to the solid solution having the organic acids adsorbed thereon to dissolve the solid solution. An organic solvent was added to extract the organic acids alone. The organic acids could be recovered in a total amount of 112 g. When an aqueous solution of $Na_2CO_3$ was added to the solid solution dissolved in sulfuric acid in an amount equivalent to the solid solution, and the mixture was stirred. There was obtained a hydrotalcite compound having the composition $Mg_5Al_2(OH)_{14}(CO_3)_{0.6}(SO_4)_{0.4} \cdot 3H_2O$. When this hydrotalcite was calcined at 600° C., it could be again used for the aforesaid treatment.

What I claim is:

1. A method for purifying cyclohexanone containing by-product organic acids and obtained by oxidation of cyclohexane, which comprises contacting said cyclohexanone with at least one treating agent selected from the group consisting of hydrotalcite compounds of the following fomula (1)

$$M_x^{2+}M_2^{3+}(OH)_{2x+6-nz}(A^{n-})_z \cdot mH_2O \qquad (1)$$

wherein $M^{2+}$ represents a divalent metal ion selected from the group consisting of $Mg^{2+}$, $Ca^{2+}$, $Zn^{2+}$, $Co^{2+}$, $Ni^{2+}$ and $Cu^{2+}$, $M^{3+}$ represents a trivalent metal ion selected from the group consisting of $Al^{3+}$, $Fe^{3+}$, $Cr^{3+}$, $Ni^{3+}$, $Co^{3+}$ and $Mn^{3+}$, $A^{n-}$ represents an anion having a valence of n and is selected from the group consisting of $Cl^-$, $Br^-$, $I^-$, $F^-$, $OH^-$, $CO_3^{2-}$, $SO_4^{2-}$, $HPO_4^{2-}$, $Fe(CN)_6^{3-}$, $Fe(CN)_6^{4-}$, $CH_3COO^-$, $(COO)_2^{2-}$, a citrate ion, a tartrate ion and a benzoate ion, and x, z and m represent numbers satisfying the following expressions $1 < x < 20$,
$0 < z \leq 2$,
$0 \leq m < 20$, and metal oxide-type solid solutions of the following formula (2)

$$M_{1-x'}^{2+}M_{x'}^{3+}O_{1+\frac{1}{2}x'} \qquad (2)$$

wherein $M^{2+}$ and $M^{3+}$ are as defined with respect to formula (1), and x' is a number represented by $0 < x' < 0.5$, and showing a powder X-ray diffraction pattern corresponding to $M^{2+}O$.

2. The method of claim wherein in formula (1), x, z and m are numbers satisfying the following expressions,
$3 \leq x \leq 8$,
$1 \leq z \leq 2$,
$0 \leq m \leq 6$.

3. The method of claim 1 wherein in formula (2), x' represents a number satisfying the following expression $0 < x' < 0.4$.

4. The method of claim 1 wherein the temperature at which the cyclohexanone is contacted with the treating agent is about 10° to about 300° C.

* * * * *